US012738367B2

(12) United States Patent
Xie et al.

(10) Patent No.: US 12,738,367 B2
(45) Date of Patent: Sep. 15, 2026

(54) BLOCKCHAIN-BASED AND HUMAN CHARACTERISTICS INTELLIGENCE RECOGNITION FOR APPOINTMENT VISUALIZATION ELDERLY CARE SYSTEM

(71) Applicants: Qingdao University of Science and Technology, Qingdao (CN); Jiangsu Zeran Information Technology Co., Ltd, Changzhou (CN)

(72) Inventors: Benju Xie, Qingdao (CN); Bowen Jiang, Qingdao (CN); Xu Huang, Qingdao (CN)

(73) Assignees: Qingdao University of Science and Technology, Qingdao (CN); Jiangsu Zeran Information Technology Co., Ltd, Changzhou (CN)

( * ) Notice: Subject to any disclaimer, the term of this patent is extended or adjusted under 35 U.S.C. 154(b) by 711 days.

(21) Appl. No.: 18/198,282

(22) Filed: May 16, 2023

(65) Prior Publication Data

US 2024/0233924 A1 Jul. 11, 2024

(30) Foreign Application Priority Data

Jan. 7, 2023 (CN) ........................ 202310022468.X

(51) Int. Cl.
*G16H 40/20* (2018.01)
*G04C 10/00* (2006.01)
(Continued)

(52) U.S. Cl.
CPC ............. *G16H 40/20* (2018.01); *G04C 10/00* (2013.01); *G04G 21/04* (2013.01); *G06V 10/24* (2022.01);
(Continued)

(58) Field of Classification Search
CPC ...... G16H 40/20; G16H 40/67; G06V 40/171; G06V 40/165; G06V 40/172; G06V 10/24;
(Continued)

(56) References Cited

U.S. PATENT DOCUMENTS 9,224,060 B1 * 12/2015 Ramaswamy ......... G06V 40/67
2003/0156199 A1 * 8/2003 Shindo ................. H04N 23/611 348/207.99
(Continued)

OTHER PUBLICATIONS

Lei, Lei, Dae-Hwan Kim, Won-Jae Park, and Sung-Jea Ko. "Face recognition using LBP Eigenfaces." IEICE Transactions on Information and Systems 97, No. 7 (2014): 1930-1932. (Year: 2014).*
(Continued)

*Primary Examiner* — David Perlman

(57) ABSTRACT

A blockchain-based and human characteristics intelligence recognition for appointment-based elderly care system includes a cloud server, a smartwatch and a management terminal, the cloud server is connected to the smartwatch and the management terminal, the smartwatch is worn on the elderly user, the management terminal includes a PC terminal, a mobile terminal and a display screen; the invention provides effective first time identification and can use the wearing device efficiently for a long time based on blockchain.

8 Claims, 10 Drawing Sheets

(51) Int. Cl.

| | |
|---|---|
| ***G04G 21/04*** | (2013.01) |
| ***G06V 10/24*** | (2022.01) |
| ***G06V 10/30*** | (2022.01) |
| ***G06V 10/36*** | (2022.01) |
| ***G06V 20/40*** | (2022.01) |
| ***G06V 40/16*** | (2022.01) |
| ***G16H 40/67*** | (2018.01) |

(52) U.S. Cl.
CPC .............. *G06V 10/30* (2022.01); *G06V 10/36* (2022.01); *G06V 20/41* (2022.01); *G06V 40/165* (2022.01); *G06V 40/171* (2022.01); *G06V 40/172* (2022.01); *G16H 40/67* (2018.01)

(58) Field of Classification Search
CPC ........ G06V 10/30; G06V 20/41; G06V 10/36; G04C 10/00; G04G 21/04
See application file for complete search history.

(56) References Cited

U.S. PATENT DOCUMENTS

| | | | | |
|---|---|---|---|---|
| 2019/0200872 | A1* | 7/2019 | Matsuoka .............. | G08B 19/00 |
| 2019/0238568 | A1* | 8/2019 | Goswami ............ | H04L 63/1416 |
| 2020/0118317 | A1* | 4/2020 | Mysore Siddu ....... | G06V 40/16 |
| 2020/0137569 | A1* | 4/2020 | Jabara .................. | H04N 21/432 |
| 2021/0004570 | A1* | 1/2021 | Zhai ...................... | G06T 7/0002 |
| 2022/0157143 | A1* | 5/2022 | Panneer Selvam .... | G04G 9/007 |
| 2023/0190140 | A1* | 6/2023 | Tiron ..................... | A61B 5/746 600/534 |
| 2023/0206700 | A1* | 6/2023 | Khan .................. | G06V 40/165 382/116 |
| 2024/0015340 | A1* | 1/2024 | Luo ...................... | G06V 40/168 |

OTHER PUBLICATIONS

Paul, Kamal Chandra. "Real-Time Low-Resolution Face Recognition using Local Binary Pattern Histograms, Eigenface, and Fisherface Algorithms." PhD diss., Texas State University, 2018. (Year: 2018).*

* cited by examiner a b a b

BLOCKCHAIN-BASED AND HUMAN CHARACTERISTICS INTELLIGENCE RECOGNITION FOR APPOINTMENT VISUALIZATION ELDERLY CARE SYSTEM

CROSS REFERENCE TO RELATED APPLICATIONS

The present application claims the benefit of Chinese Patent Application No. 202310022468.X filed on Jan. 7, 2023, the contents of which are incorporated herein by reference in their entirety.

TECHNICAL FIELD

The present invention relates to the field of elderly care systems, more specifically it relates to an appointment visualization elderly care system based on blockchain and intelligent recognition of human characteristics.

BACKGROUND

As the ageing of our population continues to accelerate, the issue of elderly care has developed into a serious social problem in China, with a significant proportion of elderly people now choosing to live alone at home. Therefore, with the gradual increase in ageing in recent years, there has been a huge social need to enable the elderly to be properly and completely cared for.

There are solutions that incorporate digital technology, such as the automatic detection of combustible gas and smoke levels, as well as the automatic determination of whether someone is intruding and whether the elderly person is acting abnormally, and then send an alarm based on the result of the detection or send an alarm message via a server for the care of elderly people living alone. In essence, however, these are extremely costly to maintain and only take into account a small proportion of the external risks associated with caring for the elderly.

This is why there is also a rise in the form of nursing homes in China, the mainstream form of care abroad. There are still major difficulties in achieving a way of enabling the elderly to link up with their families efficiently and for the family to know first-hand how the elderly are actually being cared for.

Therefore, the market is in dire need of better equipment for the elderly to avoid loss, being picked up and used at will, the need for effective first-time identification of the user, and the ability to use the equipment efficiently for long periods of time are among the many problems to be solved.

SUMMARY

The present invention overcomes the shortcomings of the prior art and provides effective first-time identification and efficient use of wearable devices for a long period of time based on blockchain and intelligent identification of human features for about-visualized elderly care systems.

The technical solution of the invention is as follows:

a blockchain and human characteristics intelligence recognition-based appointment visualization elderly care system, including a cloud server, a smartwatch and a management terminal, with the cloud server linked to the smartwatch and the management terminal, the smartwatch worn by the elderly user, and the management terminal including a PC terminal, a mobile terminal and a display screen;

a smartwatch includes a central processing module, a video capture module, a voice module, a communication module, a power module and a touch control module, the central processing module being electrically connected to the video capture module, the voice module, the communication module, the power module and the touch control module, the central processing module being connected to the cloud server via the communication module; the touch control module reading the touch operation commands on the display of the smartwatch;

a cloud server parses the data transmitted by the smartwatch and the management terminal, and uses blockchain technology for data storage and execution of the corresponding commands for the data;

a management terminal is used by service staff, supervisors, family members and customer service to facilitate understanding of the current situation of the elderly, establish mutual communication channels and push timely information on possible dangers;

Further, the central processing module matches the face image information captured by the video capture module, specifically comprising the steps of:

1.1) Data acquisition step: the video acquisition module acquires the original image of the wearer's human face features; the acquired original image is de-noised, then color-corrected, followed by face alignment, and finally cropped to obtain a pure face image;

1.2) Feature extraction step: obtain the data set after processing in step 1.1) and use $I^i$ denote the ith image of P*Q (An image of P pixels by Q pixels), and perform LBP (Local Binary Pattern) on each image to obtain a new image $$I_i^{LBP};$$

change the $$I_i^{LBP}$$

LBP is applied to each image to obtain a new image; the image is stretched into vector form and multiple images are combined into a single image matrix to generate the LBP feature space $$\{x_1^{LBP}, x_2^{LBP} \dots x_N^{LBP}\};$$

perform mean normalisation on the images and obtain $$x_{avg}^{LBP} = \frac{1}{N}\sum_{i=1}^{N} x_i^{LBP}$$

mean value of all images to generate the mean face meanface, and subtract the mean value of all images; if the image dimension is not high at this time, find its eigenvalue and eigenvector by the covariance matrix; if the image dimension is too high at this time, first calculate the $X^T \cdot X$ The eigenvalues and eigenvectors of the matrix, due to the left multiplication of $X^T \cdot X \cdot v = \lambda \cdot v$, perform a left multiplication matrix X, we get $X \cdot X^T \cdot (X \cdot v) = \lambda \cdot (X \cdot v)$, which gives that the eigenvalues of $X \cdot X^T$ are the eigenvalues of $X^T \cdot X$ and the eigenvectors are $u = X \cdot v$;

1.3) Operational processing step: sort the feature values in step 1.2) from largest to smallest, and take the first k feature values, and the corresponding first k feature vectors ($u_1$, $u_2$, $u_3$ . . . $u_k$) as the LBP Eigenface, at which point each feature vector is a feature face; thus through the new k-dimensional subspace, the original high-dimensional vector can be passed through the low-dimensional ($w_1$, $w_2$, $w_3$ . . . $w_k$) representation of a face; where the eigenvectors are P*Q dimensional vectors, the calculation $w_k$ the following equation, where u is the eigenvector, k is the subscript of k eigenvectors, and T is the computation of the symbolic transpose row:

$$w_k = u_k^T\left(x_i^{LBP} - x_{avg}^{LBP}\right).$$

Further, the denoising process of the image in step 1.1) uses median filtering, where the median filtering is a process of arranging the pixel values in order of size in a convolution frame, selecting the middle pixel value as the filtered pixel value, and cycling through all the pixel values in turn to produce the filtered image;

Color correction using histogram correction, where more concentrated areas of the histogram are split and stretched, and more dispersed areas are combined and compressed so that the pixels within a range are approximately the same;

Face Alignment acquires images containing pure face sizes by key point recognition, transforming the face.

Further, face alignment uses face_recognition for face keypoint detection to obtain 68 keypoints; then the face is rotated according to the angle between the left and right eye center coordinates and the horizontal direction to align it vertically, after alignment, and the obtained other face coordinates are similarly rotated; then the width of the face in the horizontal direction is obtained according to the leftmost and rightmost coordinates of the lower jaw respectively after alignment, and then The vertical length of the face is obtained from the ratio of the center of the eyes to the center of the mouth.

Further, a face is reconstructed by meanface+u·k, i.e. the average face+feature vector*reduced dimensional coordinates for representation.

Further, the power supply module comprises an output sampling circuit, a transient detection circuit and a fixed on-time generation circuit.

Output sampling circuitry collects the output voltage and eliminates the error between the steady state output voltage and the reference value by means of a high bandwidth op-amp, sampling the inductor current ripple instead of the output voltage ripple for control so that the output capacitor is selected as a small ESR (Equivalent Series Resistance) ceramic capacitor to improve the output ripple;

Transient detection circuitry for detecting rapid increases in load and improving transient response speed by forcing the main power tube on;

The fixed on-time generation circuit accepts control signals to generate the control signals required by the driver circuit;

An input voltage sampling circuit is provided at the converter input of the power module to detect the input voltage and serve as the input signal for the fixed on-time generation circuit, so that the system switching frequency remains approximately constant in the steady state when the input voltage changes; a current sampling circuit is provided at the inductor connected to the converter to sample the inductor current ripple information and convert it into a voltage signal to serve as the input signal for the transient detection circuit and the fixed on-time generation circuit input signals for the transient detection circuit and the fixed on-time generation circuit;

The output voltage is sampled through a voltage divider network and then adjusted with the reference voltage by a high bandwidth op-amp, and is also used as the input signal for the fixed on-time generation circuit and the transient detection circuit; the transient detection circuit compares the current ripple information with the output voltage information, and when a dramatic increase in load occurs, the modulator is controlled to force the upper tube on until it is detected again. $V_{comp} > V_{iL}$, at which point the modulator is controlled to force the upper tube on until it is redetected $V_{comp} < V_{iL}$ The modulator is then controlled to turn the upper tube on forcibly until it is detected again, restoring steady-state COT control, thus achieving an approximate single-cycle transient response; where $V_{comp}$ is the error amplification signal of the output voltage after the operational amplifier, and $V_{iL}$ is the ripple voltage signal obtained from the inductor current sampling and conversion.

Further, the power supply module further comprising a driver circuit, a converter B, an inductor L, a capacitor C, a resistor R and a MOS tube.

The input of converter B is connected to the input voltage sampling circuit, and the input voltage sampling circuit is connected to the fixed on-time generation circuit, and the other input of converter B is connected to MOS tube S1, and the gate of MOS tube S1 is connected to the driver circuit; the output of converter B is connected to MOS tube S2 and MOS tube S3, and the gate of MOS tube S2 and the gate of MOS tube S3 are connected to the driver circuit; the source of MOS tube S3 is connected to inductor L, and the output sampling circuit is connected to the transient detection circuit and the fixed on-time generation circuit, and the fixed on-time generation circuit is connected to the driver circuit. The source of MOS tube S3 is connected to inductor L, and the output sampling circuit is connected to inductor L. The output sampling circuit is connected to the transient detection circuit and the fixed on-time generation circuit, and the fixed on-time generation circuit is connected to the driver circuit and the transient detection circuit.

Wherein, one end of the inductor L is connected to one end of the inductor C and one end of the resistor R, the other end of the inductor C and the other end of the resistor R are grounded together, and the inductor C and the resistor R form a voltage divider network.

Further, the output sampling circuit comprises a resistor, a capacitor, an operational amplifier and a comparator.

One end of capacitor Cs is connected to one end of resistor R3 and the other end of capacitor Cs is connected to one end of resistor R1 and is used as the two differential sampling input pins for the output sampling circuit.

The other end of resistor R1 is connected to one end of resistor R2, the positive terminal of telecom amplifier U2, and the other end of resistor R2 is grounded; the other end of resistor R3 is connected to one end of resistor R4, the negative terminal of telecom amplifier U2, and the other end of resistor R4 is used as an external pin together with the output of telecom amplifier U2 and is connected to one end of comparator U3.

The other end of resistor RFBT is connected to one end of resistor R5, one end of operational amplifier U5 as the sampling input pin of the output sampling circuit, the other end of operational amplifier U5 is connected to the reference voltage Vref, the other end of resistor R5 is connected to one end of capacitor C1, the other end of capacitor C1 is connected as an external pin together with the output of operational amplifier U5 and is connected to the other end of comparator U3, the output of comparator U3 is used as the other external pin.

Further, the output sampling circuit is externally designed with one end of the inductor L connected to one end of the resistor Rs, the other end of the inductor L connected to one end of the capacitor Cs, one end of the capacitor Cout, and one end of the resistor RFBT, and the other end of the resistor Rs connected to the other end of the capacitor Cs; the other end of the capacitor Cout is grounded together with one end of the resistor RFBB, and the other end of the resistor RFBB is connected to the resistor the other end of the RFBT is connected to the other end of the RFBT.

The output sampling circuit consists of two parts: inductor current and output voltage sampling. The inductor current sampling design needs to satisfy the following equation:

$$R_s \cdot C_s = i_L / R_{DCR}$$

where $R_{DCR}$ is the inductor DC resistance, which converts the inductor current into $C_s$ voltage on the inductor and connects it to the two inputs of the telecom amplifier $U_2$, the telecom amplifier $U_2$ converts the differential signal to output relative to the reference ground and connects it to the inverting input of the comparator $U_3$ and the input of the bias voltage.

The beneficial effects of the present invention are:

(1) The solution uses a unique LBP combined with the Eigenface method, which improves recognition rates significantly in environments with highly variable lighting conditions. This results in efficient first time ID recognition.

(2) The solution is one of the important research directions to design a closed-loop control system for miniature power supply modules in order to improve the usage time of the worn devices. The control circuit designed in this solution eliminates the steady-state error due to ripple voltage valley conduction by amplifying the error between the output voltage feedback value and the reference value using an operational amplifier; replaces the output voltage ripple with the sampled inductor current ripple, thus getting rid of the dependence on large ESR output capacitors; detects the moment when a violent load jump occurs through a comparator and forces the main power tube to be continuously on, achieving an approximate The single cycle response improves the transient response speed and also enables the power supply to be used for a longer period of time and reduces the possibility of such maintenance.

DETAILED DESCRIPTION OF EMBODIMENTS

Figure 1:
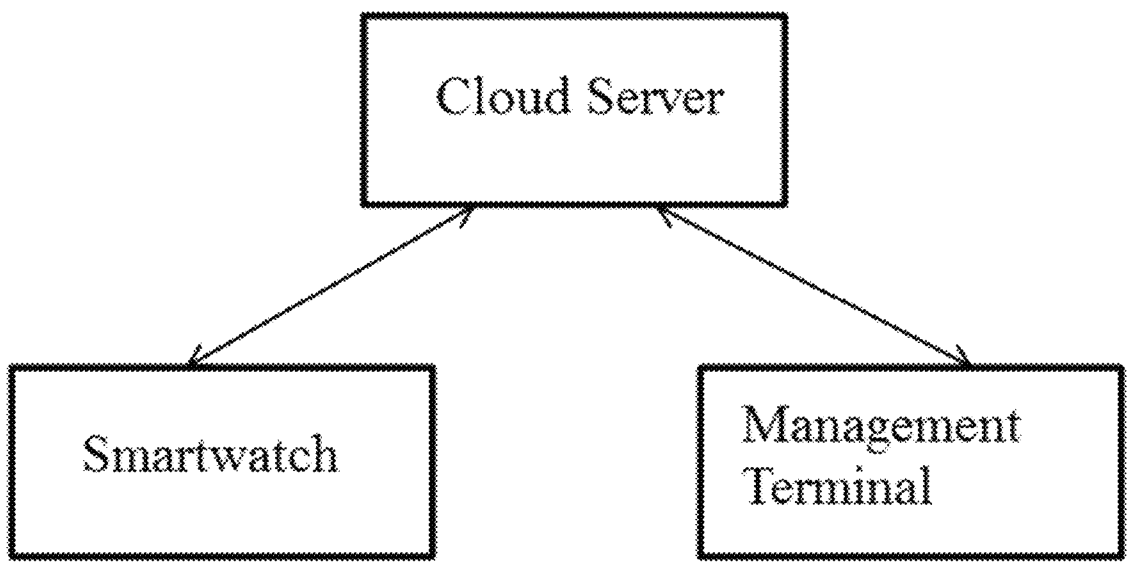
FIG. 1 shows a schematic diagram of the system of the present invention.
Figure 2:
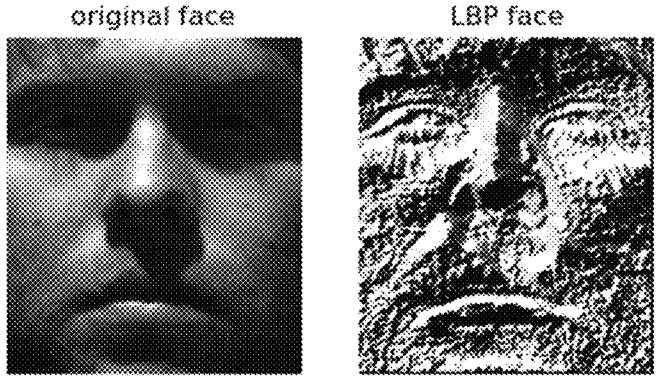
FIG. 2 shows a graph of the changes after the LBP treatment of the present invention.
Figure 3:
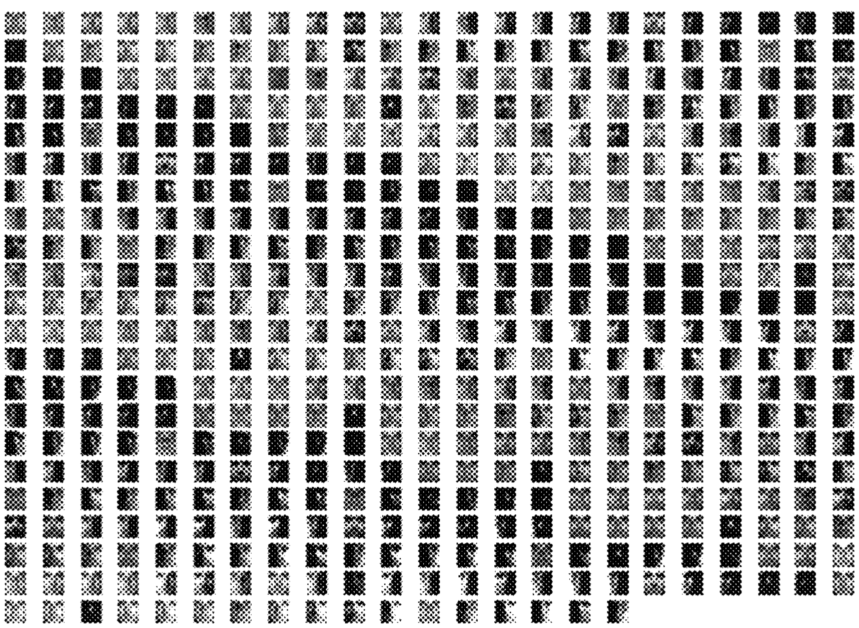
FIG. 3 shows a schematic diagram of the Yale Extended Face Database B (B+) of the present invention.

The embodiments of the present invention are described below through specific examples, and a person skilled in the art can easily understand other advantages and effects of the present invention from the contents disclosed in the specification. The present invention can also be implemented or applied through other different specific embodiments, and various details in this specification can also be modified or changed based on different viewpoints and applications without departing from the spirit of the present invention. It should be noted that the following embodiments and features in the embodiments may be combined with each other under the condition of no conflict.

It should be noted that the drawings provided in the following embodiments are only used to illustrate the basic concept of the present invention in a schematic way, so the drawings only show the components related to the present invention rather than the amount, shapes and sizes of components in an actual implementation. In the actual implementation, the type, quantity and ratio of each component can be changed at will, and the layout of the components may also be more complicated.

As shown in FIGS. 1 to 11, the blockchain-based and human characteristics intelligence recognition of the about-vision elderly system, including a cloud server, a smart watch and a management terminal, the cloud server linked to the smart watch and the management terminal, the smart watch is worn by the elderly user, and the management terminal includes a PC terminal, a mobile terminal and a display screen.

The smartwatch includes a central processing module, a video capture module, a voice module, a communication module, a power module and a touch control module; the central processing module is electrically connected to the video capture module, the voice module, the communication module, the power module and the touch control module; the central processing module is connected to the cloud server via the communication module; the touch control module reads the touch operation commands on the display of the smartwatch; the user can The user can use the smartwatch to make calls, videos and display the current status of the user directly.

The cloud server parses the data transmitted by the smartwatch and the management terminal, and uses blockchain technology for data storage and execution of the corresponding instructions for the data; the use of blockchain technology avoids data tampering and better safeguards the actual situation response.

The management terminal is used by service staff, supervisors, family members and customer service to facilitate understanding of the current situation of the elderly, establish mutual communication channels and push timely information on possible dangers.

The central processing module matches the face image information captured by the video capture module to ensure that the identity of the user is accurate, and also to safeguard the device from being lost, or picked up by others and used at will. Specific face image feature extraction includes the following steps:

1.1) Data acquisition steps: The video acquisition module acquires the original image of the wearer's human face features; the acquired original image is de-noised, then color corrected, followed by face alignment, and finally cropped to obtain a pure face image.

The image is denoised using median filtering, which is the process of arranging the pixel values in order of size in a convolution frame, selecting the middle pixel value as the filtered pixel value, and cycling through all the pixel values in turn to produce the filtered image.

Color correction using histogram correction, where more concentrated areas of the histogram are split and stretched, and more dispersed areas are combined and compressed so that the pixels within a range are approximately the same.

Face Alignment acquires images containing pure face sizes by key point recognition, transforming the face.

The face is aligned using face_recognition for face keypoint detection, and 68 keypoints are obtained; then the face is rotated according to the angle between the left and right eye center coordinates and the horizontal direction, so that it is aligned vertically, after alignment, and the other face coordinates obtained are also rotated; then the width of the face in the horizontal direction is obtained according to the leftmost and rightmost coordinates of the jaw after alignment, and then the length of the face in the vertical direction is obtained according to the ratio of the two eye centers to the center of the mouth as a whole. The vertical length is then obtained from the ratio of the center of the eyes to the center of the mouth.

1.2) Feature extraction step: obtain the data set after processing in step 1.1) and use $I^i$ denote the ith image of P*Q, and perform LBP on each image to obtain a new image $I_i^{BP}$; change the $I_i^{BP}$ LBP is applied to each image to obtain a new image; the image is stretched into vector form and multiple images are combined into a single image matrix to generate the LBP feature space $$\{x_1^{LBP}, x_2^{LBP} \ldots x_N^{LBP}\};$$

perform mean normalisation on the images and obtain $$x_{avg}^{LBP} = \frac{1}{N}\sum\nolimits_{i=1}^{N} x_i^{LBP}$$

mean value of all images to generate the mean face meanface, and subtract the mean value of all images; if the image dimension is not high at this time, find its eigenvalue and eigenvector by the covariance matrix; if the image dimension is too high at this time, first calculate the $X^T \cdot X$ The eigenvalues and eigenvectors of the matrix, due to the left multiplication of $X^T \cdot X \cdot v = \lambda \cdot v$, perform a left multiplication matrix X, we get $X \cdot X^T \cdot (X \cdot v) = \lambda \cdot (X \cdot v)$, which gives $X \cdot X^T$ The eigenvalues are the $X^T \cdot X$ the eigenvalues and the eigenvectors are $u = X \cdot v$ the (1.3) Operational processing step: sort the feature values in step 1.2) from largest to smallest, and take the first k feature values, and the corresponding first k feature vectors ($u_1, u_2, u_3 \ldots u_k$) as the LBP Eigenface, at which point each feature vector is a feature face; thus through the new k-dimensional subspace, the original high-dimensional vector can be passed through the low-dimensional ($w_1, w_2, w_3 \ldots w_k$) representation of a face; where the eigenvectors are P*Q dimensional vectors, the calculation $w_k$ the following equation.

$$w_k = u_k^T\left(x_i^{LBP} - x_{avg}^{LBP}\right).$$

Reconstructing a face by meanface+u·k the average face+feature vector*reduced dimensional coordinates. The system accordingly obtains the data features of each face separately for comparison to confirm the identity of the wearer.

This face recognition approach is processed with the Yale face database and the Yale extended face database B(B+) as examples. It is observed that on the light-sensitive dataset Yale Extended Face Database B(B+), LBP combined with Eigenface achieves superior performance than Eigenface in both cases. Before LBP processing, the lowest recognition rate for faces under each classifier dropped surprisingly to about 2%-3%, which was almost close to a total error state. However, after LBP processing, the recognition rates were all above 99%, close to 100%, and the highest recognition rates under different classifiers were also improved by about 10% on average.

In the Yale face database, the improvement in recognition rate is not as pronounced as in the Yale extended face database B (B+), especially on the CNN (Convolutional Neural Networks) classifier. However, overall, there is still a further improvement over the common feature extraction approach. Also, it is worth noting that the highest recognition rate for SVM (Support Vector Machine) in the Yale face database is surprisingly 100%, which exceeds the highest value of 99.67% in the extended Yale database.

The results of the specific statistics of the highest recognition rate table 1 and the lowest high recognition rate table 2 are as follows:

TABLE 1

| | Eigenface | | | LBP + Eigenface | | |
|---|---|---|---|---|---|---|
| Classifier | KNN | SVM | CNN | KNN | SVM | CNN |
| Yale face | 76.88% | 87.65% | 96.35% | 99.67% | 99.39% | 99.39% |
| extended Yale face | 80% | 96.67% | 96.67% | 85.45% | 100% | 96.67% |

TABLE 2

| | Eigenface | | | LBP + Eigenface | | |
|---|---|---|---|---|---|---|
| Classifier | KNN | SVM | CNN | KNN | SVM | CNN |
| Yale face extended | 2.61% | 4.45% | 3.64% | 99.54% | 99.39% | 98.38% |
| Yale face | 50.91% | 40.00% | 50.00% | 69.70% | 96.67% | 90.00% |

Figure 4:
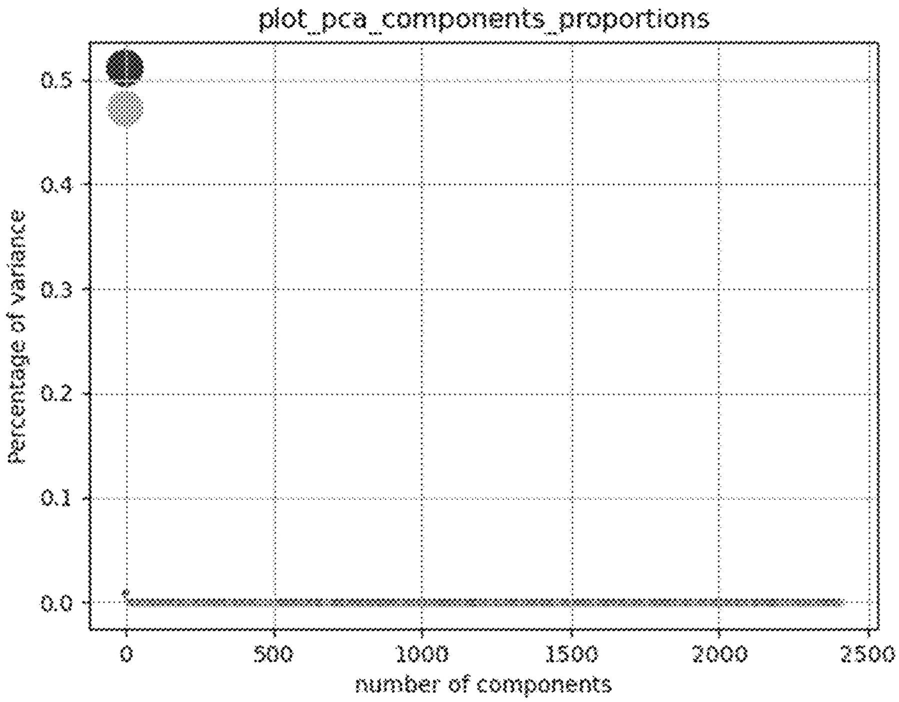
FIG. 4 shows the variance ratio plot of the eigenvalues under Eigenface of the present invention and the b-plot shows the variance ratio plot of the eigenvalues under Eigenface combined with LBP, where "components" as indicated on the horizontal axis are Number of eigenvalue components selected.
Figure 4:
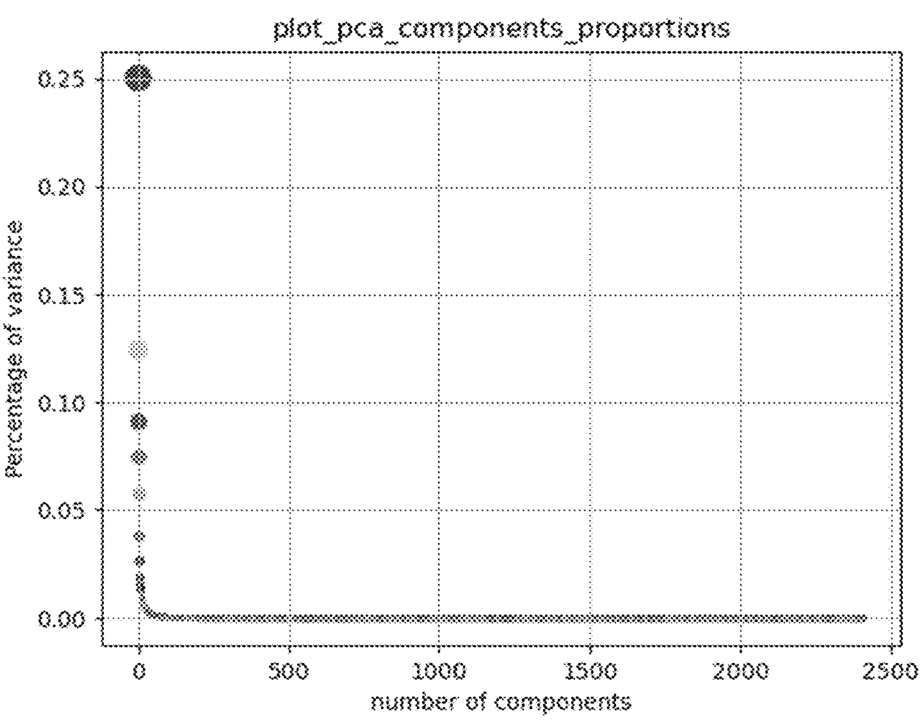
Figure 5:
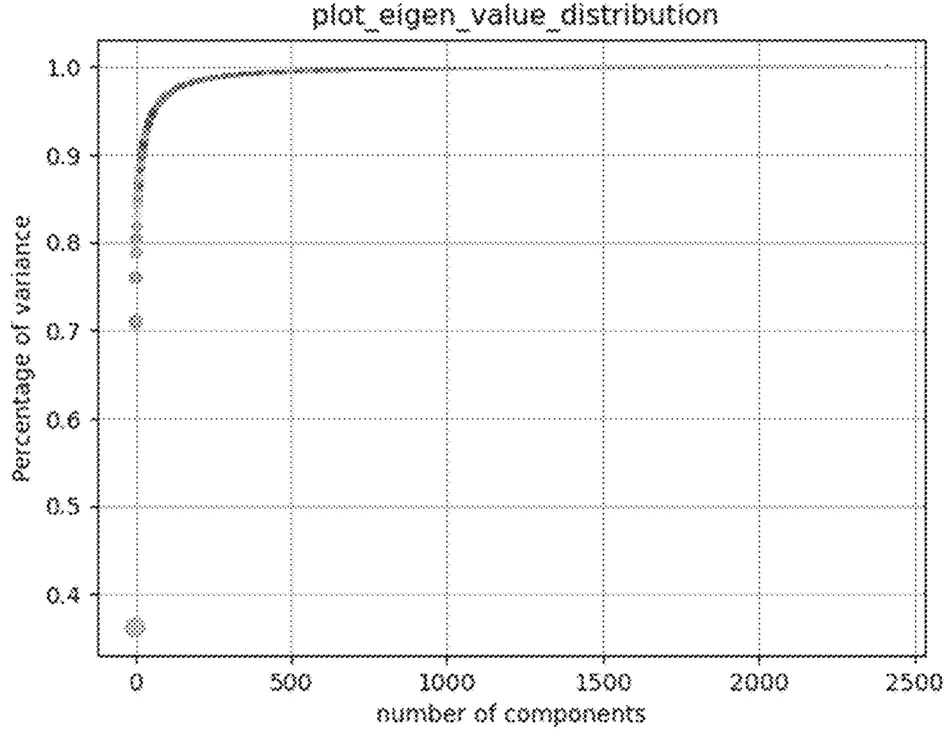
FIG. 5 shows a plot of the first n eigenvalues as a percentage of all eigenvalues under Eigenface of the present invention; the b-plot is a plot of the first n eigenvalues as a percentage of all eigenvalues under Eigenface combined with LBP.
Figure 5:
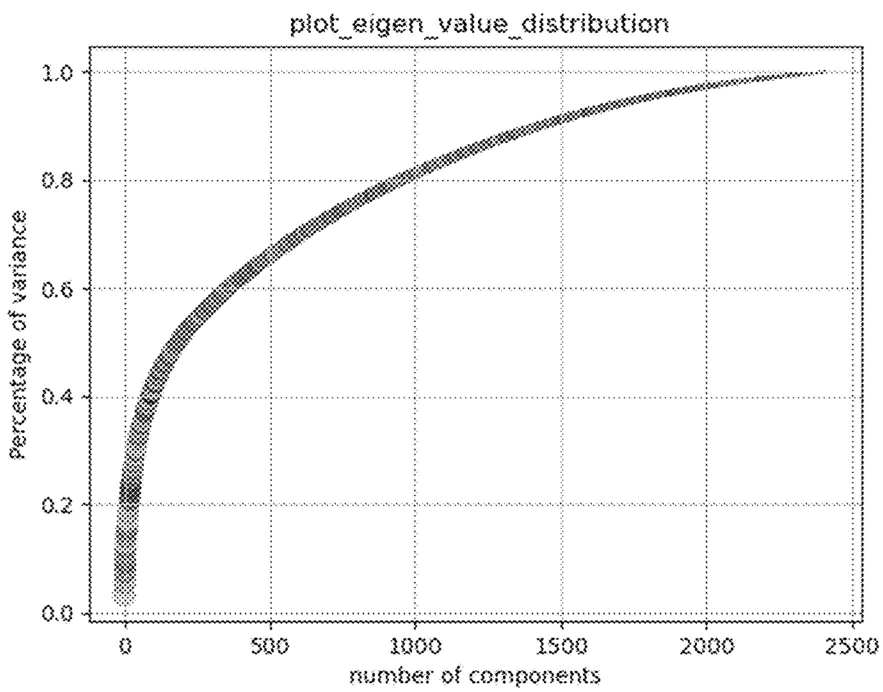
Figure 6:
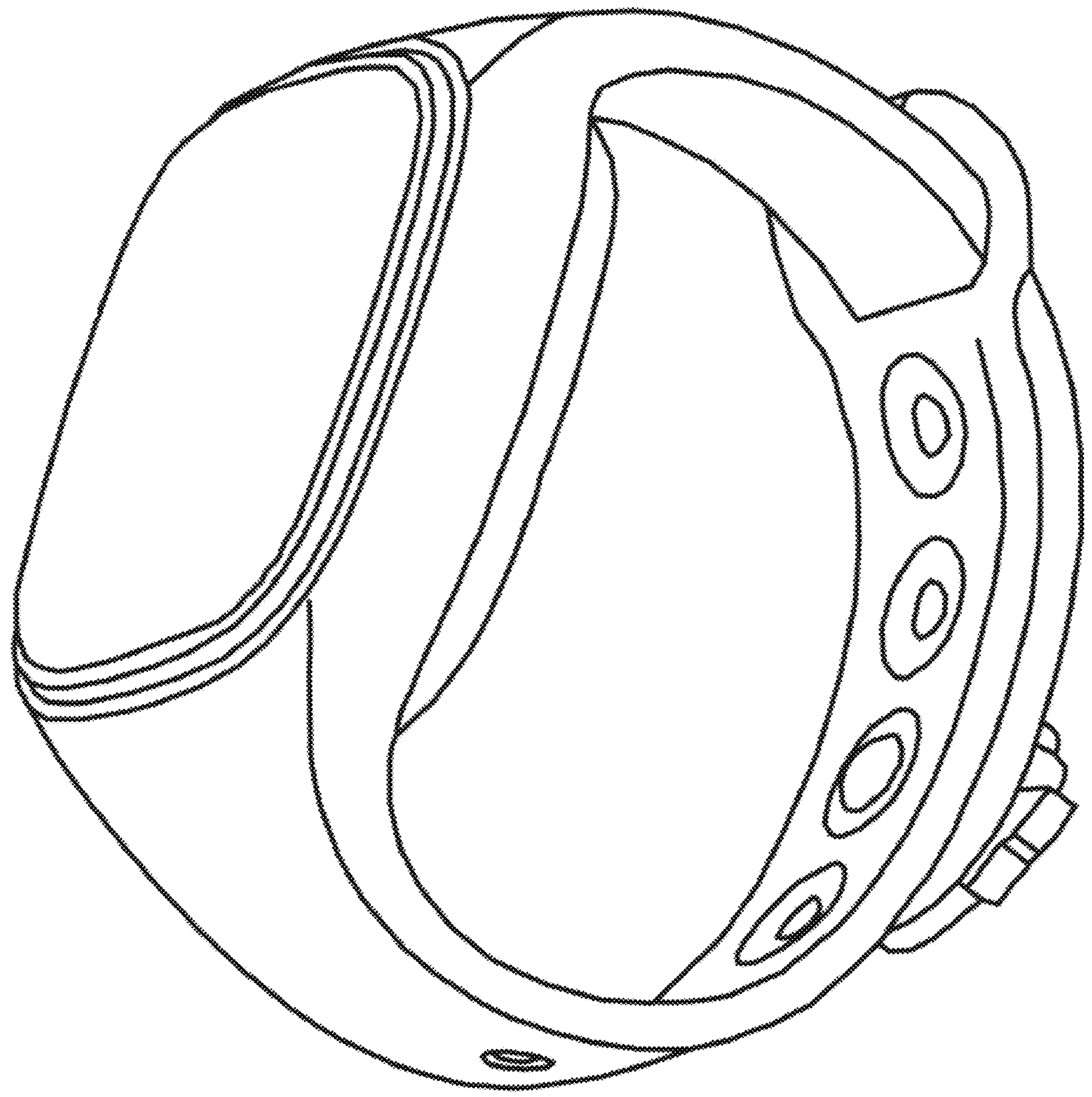
FIG. 6 shows a schematic diagram of the smartwatch of the present invention.
Figure 7:
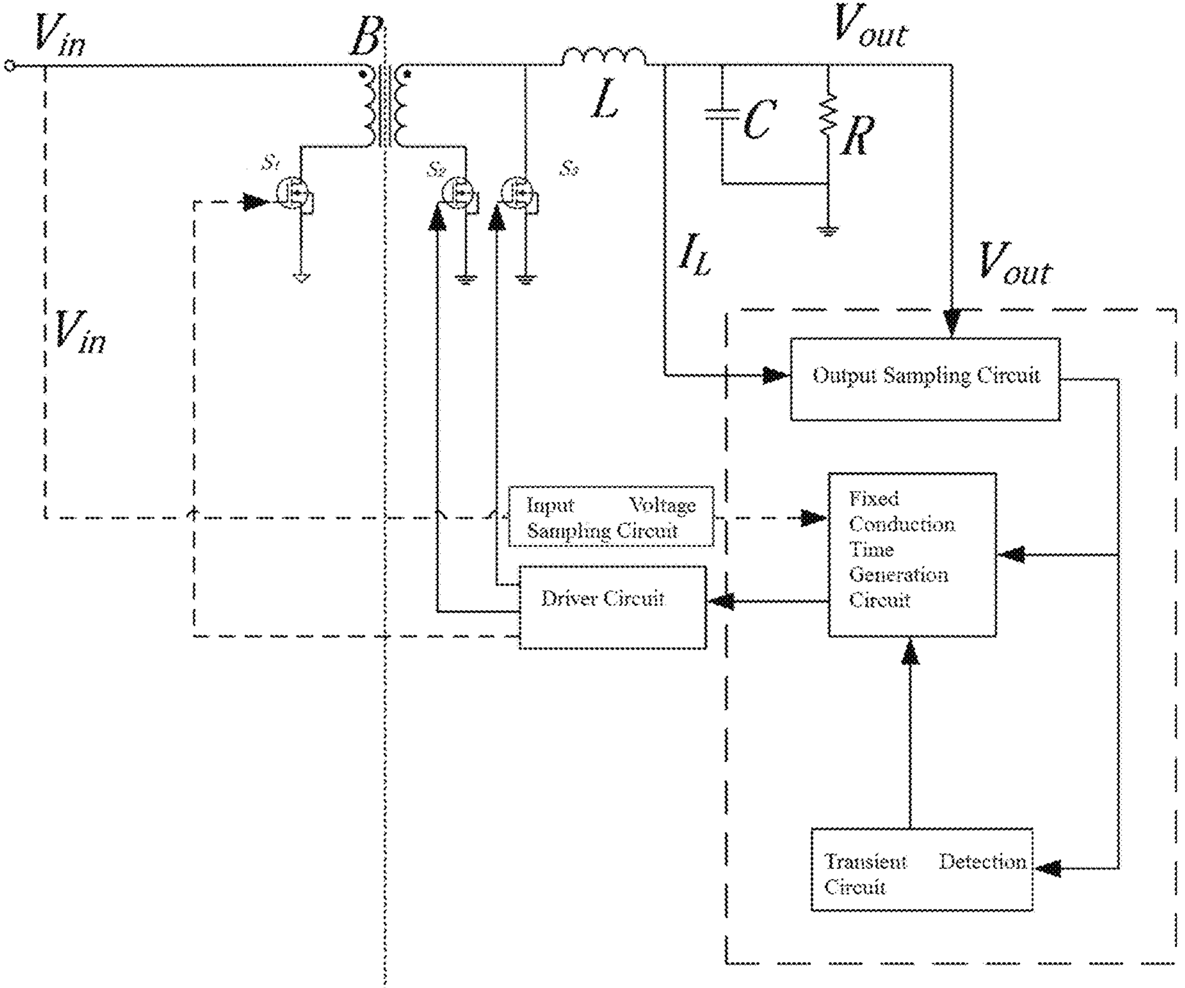
FIG. 7 shows the general circuit architecture of the power supply module of the present invention; the FIG. 8 shows a key waveform plot of the transient response of FIG. 7.

Looking (K-Nearest Neighbor) at FIGS. 4 and 5 it is clear that the feature values extracted without LBP processing are too homogenous, with the variance ratio accounted for by the top 10 feature values being too high and only a few feature vectors being extracted from multiple face images. This phenomenon leads to an imbalance in the representation of other faces where one feature face dominates absolutely. With the addition of LBP, local processing of low-exposure faces homogenizes each face, thus appropriately increasing the weight of the remaining feature faces and optimizing face recognition.

Figure 8:
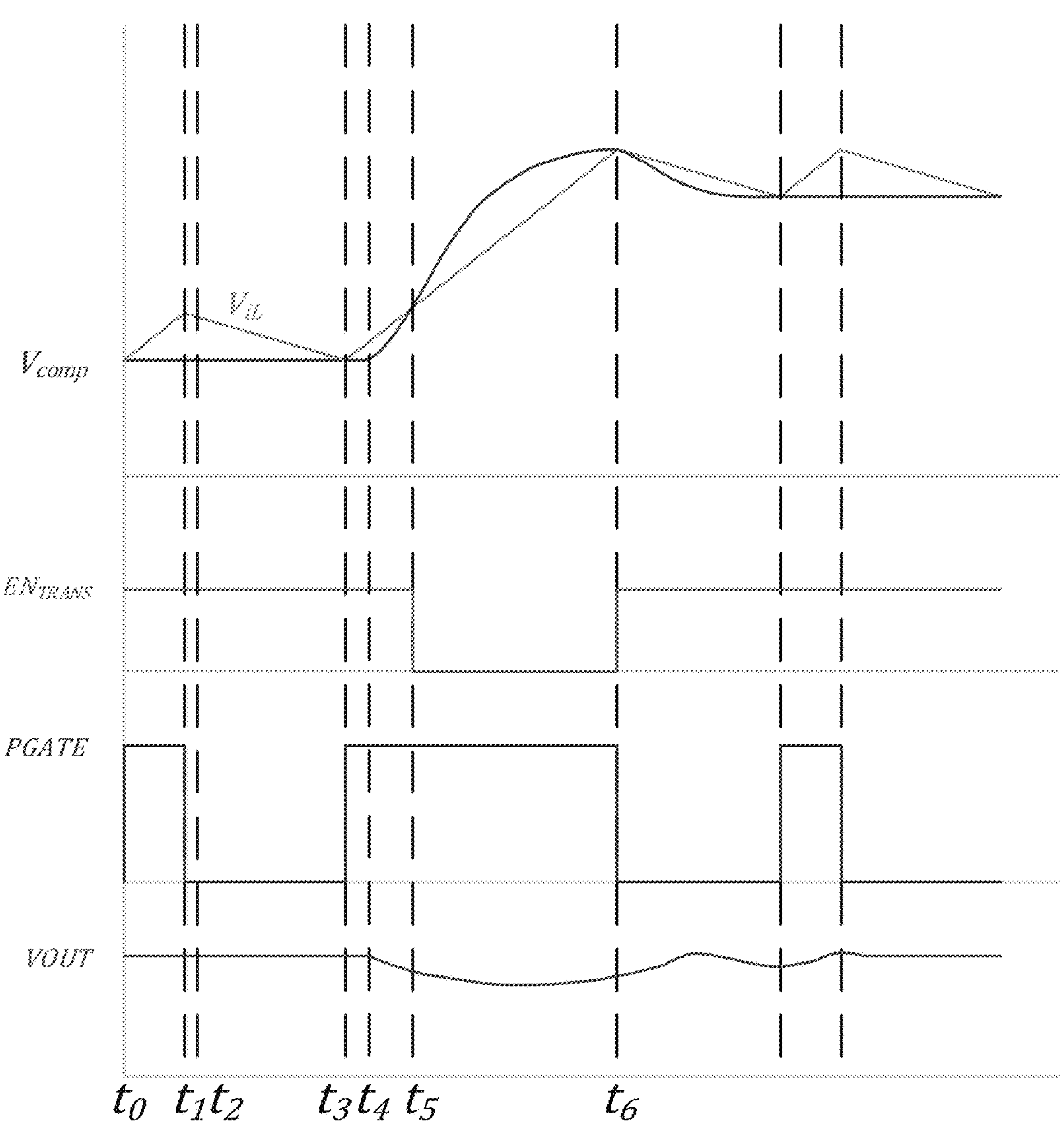
Figure 9:
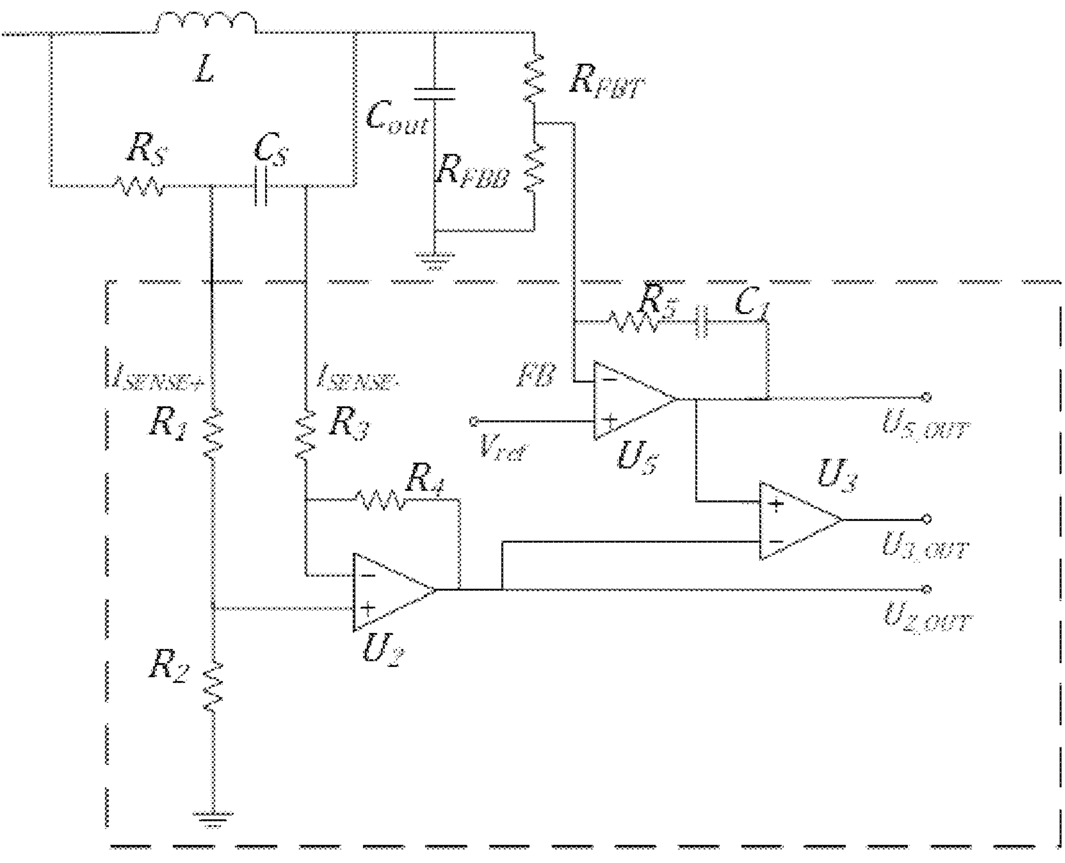
FIG. 9 shows the output sampling circuit diagram of FIG. 7.

Specifically, the power supply module includes an output sampling circuit, a transient detection circuit and a fixed on-time generation circuit. As shown in FIG. 8, the key waveform for the improved transient response proposed by this solution, where $V_{comp}$ is the error amplified signal from the output voltage after the operational amplifier, and $V_{iL}$ is the ripple voltage signal obtained by sampling the inductor current and converting EN TRANS is the transient detection signal used to control the forced conduction of the power tube, and PGATE is the primary power tube gate drive signal in the single-tube flyback topology shown in FIG. 7, and VOUT is the output voltage signal in the single-tube flyback topology shown in FIG. 7.

Output sampling circuitry collects the output voltage and eliminates the error between the steady state output voltage and the reference value by means of a high bandwidth op-amp, sampling the inductor current ripple instead of the output voltage ripple for control so that the output capacitor is selected as a small ESR ceramic capacitor to improve the output ripple.

Transient detection circuitry for detecting rapid increases in load and improving transient response speed by forcing the main power tube on.

The fixed on-time generation circuit accepts control signals to generate the control signals required by the driver circuit.

An input voltage sampling circuit is provided at the converter input of the power supply module to detect the input voltage and serve as the input signal for the fixed on-time generation circuit, so that the system switching frequency remains approximately constant in the steady state when the input voltage changes; a current sampling circuit is provided at the inductor connected to the converter to sample the inductor current ripple information and convert it into a voltage signal to serve as the input signal for the transient detection circuit and the fixed on-time generation circuit; and input signals for the transient detection circuit and the fixed on-time generation circuit.

The output voltage is sampled through a voltage divider network and then adjusted with the reference voltage by a high bandwidth op-amp, and is also used as the input signal for the fixed on-time generation circuit and the transient detection circuit; the transient detection circuit compares the current ripple information with the output voltage information, and when a dramatic increase in load occurs, the modulator is controlled to force the upper tube on until it is detected again. $V_{comp}>V_{iL}$, at which point the modulator is controlled to force the upper tube on until it is redetected $V_{comp}<V_{iL}$. The transient detection circuit is used to compare the current ripple information with the output voltage information. $V_{comp}$ is the error amplification signal of the output voltage after the operational amplifier, and $V_{iL}$ is the ripple voltage signal obtained from the inductor current sampling and conversion.

The power supply module also comprises the driver circuit, the converter B, the inductor L, the capacitor C, the resistor R and the MOS tube.

The input of converter B is connected to the input voltage sampling circuit, and the input voltage sampling circuit is connected to the fixed on-time generation circuit, and the other input of converter B is connected to MOS tube S1, and the gate of MOS tube S1 is connected to the driver circuit; the output of converter B is connected to MOS tube S2 and MOS tube S3, and the gate of MOS tube S2 and the gate of MOS tube S3 are connected to the driver circuit; the source of MOS tube S3 is connected to inductor L, and the output sampling circuit is connected to the transient detection circuit and the fixed on-time generation circuit, and the fixed on-time generation circuit is connected to the driver circuit. The source of MOS tube S3 is connected to inductor L, and the output sampling circuit is connected to inductor L. The output sampling circuit is connected to the transient detection circuit and the fixed on-time generation circuit, and the fixed on-time generation circuit is connected to the driver circuit and the transient detection circuit.

One end of the inductor L is connected to one end of the inductor C and one end of the resistor R. The other end of the inductor C and the other end of the resistor R are grounded together and the inductor C and the resistor R form a voltage divider network.

Output sampling circuit comprising resistors, capacitors, operational amplifiers and comparators.

One end of capacitor Cs is connected to one end of resistor R3 and the other end of capacitor Cs is connected to one end of resistor R1 and is used as the two differential sampling input pins for the output sampling circuit.

The other end of resistor R1 is connected to one end of resistor R2, the positive terminal of telecom amplifier U2, and the other end of resistor R2 is grounded; the other end of resistor R3 is connected to one end of resistor R4, the negative terminal of telecom amplifier U2, and the other end of resistor R4 is used as an external pin together with the output of telecom amplifier U2 and is connected to one end of comparator U3.

The other end of resistor RFBT is connected to one end of resistor R5, one end of operational amplifier U5 as the sampling input pin of the output sampling circuit, the other end of operational amplifier U5 is connected to the reference voltage Vref, the other end of resistor R5 is connected to one end of capacitor C1, the other end of capacitor C1 is connected as an external pin together with the output of operational amplifier U5 and is connected to the other end of comparator U3, the output of comparator U3 is used as the other external pin.

The output sampling circuit is externally designed with one end of inductor L connected to one end of resistor Rs, the other end of inductor L connected to one end of capacitor Cs, one end of capacitor Cout, one end of resistor RFBT, the other end of resistor Rs connected to the other end of capacitor Cs; the other end of capacitor Cout is grounded together with one end of resistor RFBB, the other end of resistor RFBB is connected to the other end of resistor RFBT the other end of the resistor RFBB is connected to the other end of the resistor RFBT.

The output sampling circuit consists of two parts: inductor current and output voltage sampling. The inductor current sampling design needs to satisfy the following equation.

$$R_s \cdot C_s = i_L / R_{DCR}$$

where $R_{DCR}$ is the inductor DC resistance, which converts the inductor current into $C_s$ voltage on the inductor and connects it to the two inputs of the telecom amplifier $U_2$, the telecom amplifier $U_2$ converts the differential signal to output relative to the reference ground and connects it to the inverting input of the comparator $U_3$ and the input of the bias voltage.

Figure 10:
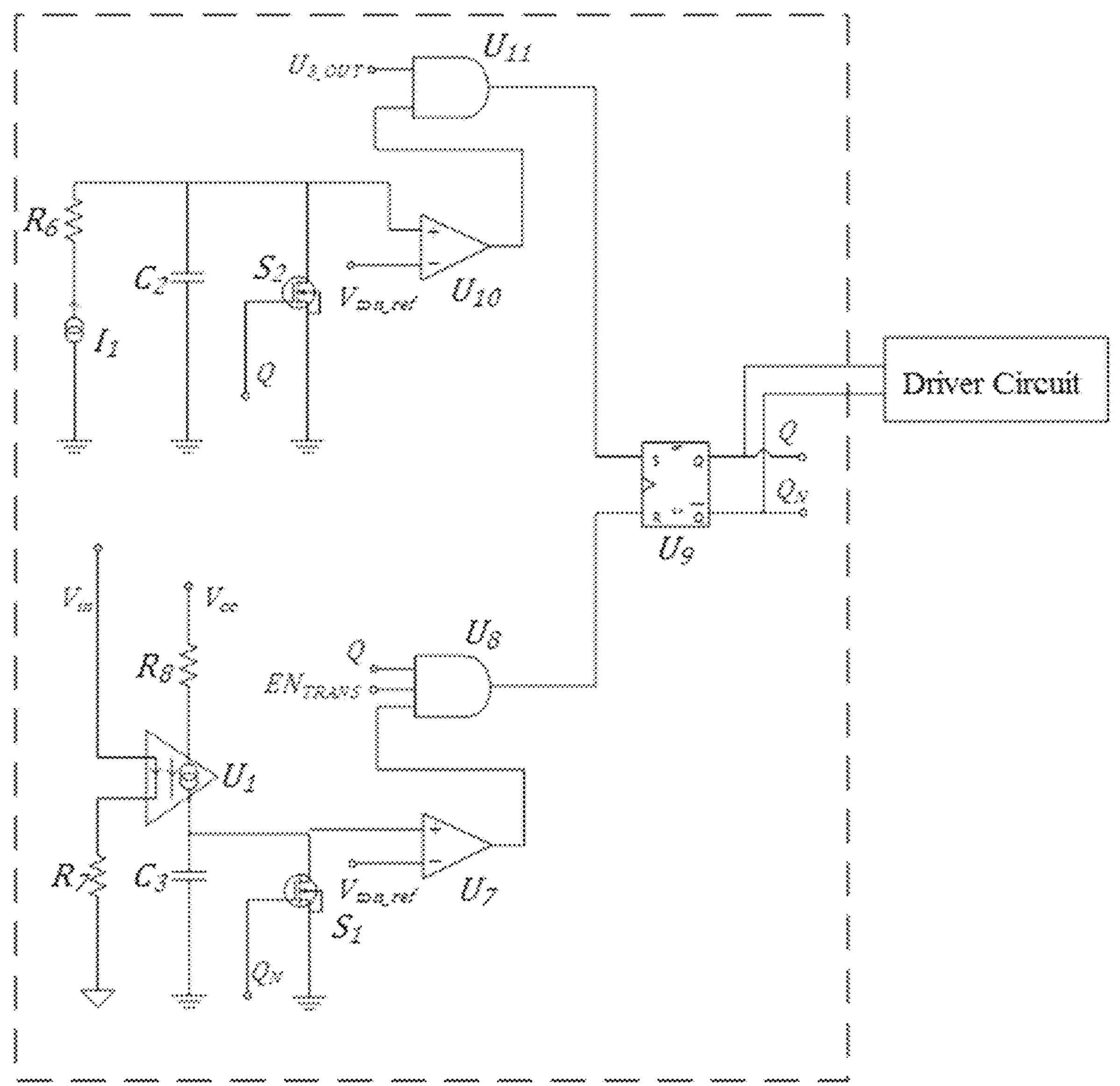
FIG. 10 shows a diagram of the fixed on-time generation circuit of FIG. 7.
Figure 11:
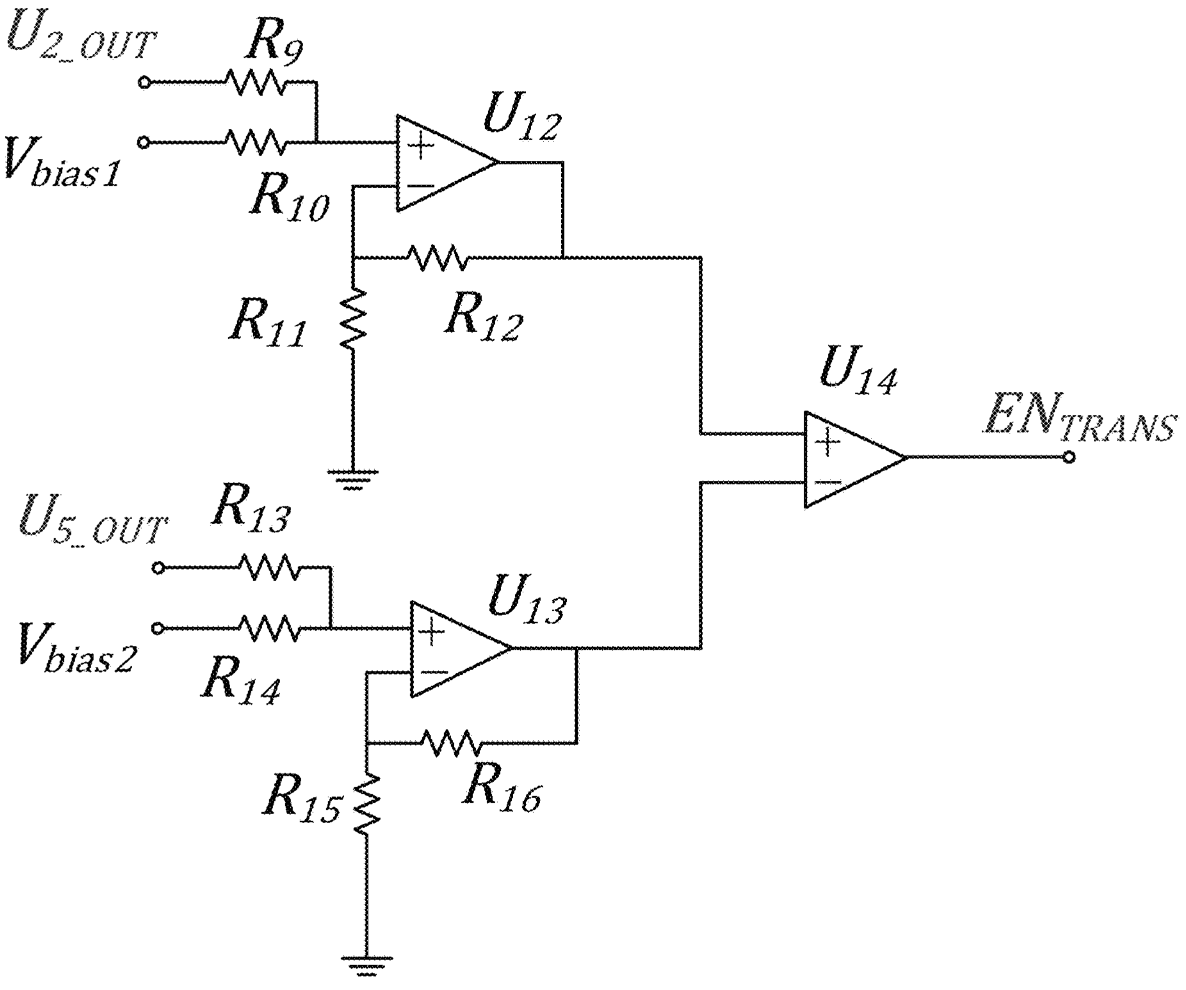
FIG. 11 shows the transient detection circuit diagram of FIG. 7.

A fixed on-time generation circuit is shown in FIG. 10. Input voltage sampling converts the input voltage through a resistor $R_7$ converted to a current signal connected to the optocoupler $U_1$ diode anode for feedback to the secondary side, and the sampling signal from the optocoupler $U_1$CE The sampled signal from the optocoupler terminal is connected to the fixed on-time generation circuit to achieve a steady-state switching frequency follows the fixed on-time ton and the steady-state switching frequency is kept approximately constant by adjusting the fixed on-time at steady-state. The steady state switching frequency is kept approximately constant by adjusting the fixed on-time during steady state.

Transient detection circuit comprising resistors, operational amplifiers and comparators.

One end of resistor R9 is connected to the output of telecom amplifier U2, one end of resistor R10 is connected to bias voltage Vbias1, the other end of resistor R9 and the other end of resistor R10 are connected together to one end of operational amplifier U12, the other input of operational amplifier U12 is connected to one end of resistor R11 and one end of resistor R12, the other end of resistor R11 is grounded, and the other end of R12 is connected to the input of comparator U14 together with the output of operational amplifier U12.

One end of resistor R13 is connected to the output of telecom amplifier U5, one end of resistor R14 is connected to the bias voltage Vbias2, the other end of resistor R13 and the other end of resistor R14 are connected together to one end of operational amplifier U13, the other input of operational amplifier U13 is connected to one end of resistor R15 and one end of resistor R16, the other end of resistor R15 is grounded and the other end of R16 is connected together with the output of operational amplifier U13 to the other input of comparator U14.

One of the operational amplifiers, U12, has a voltage biasing effect to avoid errors that can produce a false response and set the transient triggering conditions by setting the difference between the two sets of voltage biases.

In conjunction with FIG. 8, the $t_0$~$t_1$ time period, the load conditions are constant and the circuit is in steady-state COT control and in a fixed time conduction phase. The inductor current rises during this phase and $t_i$ At the time, the fixed on-time is reached and $U_7$, the $U_8$ are output high, the RS flip-flop $U_9$ output is cleared to zero and the primary edge switching tube is switched off;

in $t_1$~$t_3$ time period, the primary side switching tube turns off, the inductor current drops and the current source $I_1$ to the capacitor $C_2$ charging; $t_2$, at the moment, the minimum off time limit is reached and the comparator $U_{10}$ output is pulled high; in $t_3$ time period, the op-amp $U_2$ output is lower than the $U_5$ output, i.e., the sampled inductor current signal is less than the voltage error amplification signal, and the comparator $U_3$ output is pulled high, with the logic gate $U_{11}$ output is pulled high, the RS flip-flop $U_9$ output is pulled high and the primary edge switch tube is re-conducted;

$t_4$, the load current increases at the moment when the system is still under steady-state COT control, with the primary switching tube on for a fixed duration and the off duration limited by the minimum off time;

$t_5$, at the moment, the comparator $U_{14}$ detects that the input at the inverted end is higher than the input at the same end, the output is pulled low and the logic gate $U_8$ corresponding input is low, no clear signal is issued and the switching tube continues to conduct.

$t_6$, at the moment, the comparator $U_{14}$ detects that the input at the inverted end is again lower than the input at the in-phase end, the output is high and COT control is resumed.

in summary, the power supply module is free from the dependence of traditional COT control methods on large ESR output capacitors and has virtually no steady-state error. In comparison to COT control, the transient response detection and control of this solution can reduce the load jump down by as much as 65%, all other things being equal.

In summary, this solution's blockchain-based and human characteristics intelligence recognition of about-visualized elderly care system addresses the key user-side needs of rapid information matching and long hours of normal functioning equipment.

The above description is a specific example of the present invention, and does not constitute any limitation to the present invention. Obviously, for a person skilled in the art, after understanding the content and principles of the present invention, various modifications and changes in form and details may be made without departing from the principles and structures of the present invention, but these modifications and changes based on the inventive concept of the present invention still fall within the protection scope of the claims of the present invention.

What is claimed is:

1. A blockchain and human characteristics intelligence recognition-based appointment-based elderly care system:

including a cloud server, a smartwatch and a management terminal, with the cloud server linked to the smartwatch and the management terminal, the smartwatch worn by the elderly user, and the management terminal including a PC terminal, a mobile terminal and a display screen;

wherein the smartwatch includes a central processing module, a video capture module, a voice module, a communication module, a power module and a touch control module, the central processing module being electrically connected to the video capture module, the voice module, the communication module, the power module and the touch control module, the central processing module being connected to the cloud server via the communication module; the touch control module reading the touch operation commands on the display of the smartwatch;

the cloud server parses the data transmitted by the smartwatch and the management terminal, and uses blockchain technology for data storage and execution of the corresponding commands for the data;

the management terminal is used by service staff, supervisors, family members and customer service to facilitate understanding of the current situation of the elderly, establish mutual communication channels and push timely information on possible dangers;

wherein the power supply module comprises an output sampling circuit, a transient detection circuit and a fixed on-time generation circuit;

the output sampling circuitry collects the output voltage and eliminates the error between the steady state output voltage and the reference value by means of a high bandwidth op-amp, sampling the inductor current ripple instead of the output voltage ripple for control so that the output capacitor is selected as a small ESR ceramic capacitor to improve the output ripple;

the transient detection circuitry detects rapid increases in load and improves transient response speed by forcing the main power tube on;

the fixed on-time generation circuit accepts control signals to generate the control signals required by the driver circuit;

wherein an input voltage sampling circuit is provided at the converter input of the power module to detect the input voltage and serve as the input signal for the fixed on-time generation circuit, so that the system switching frequency remains approximately constant in the steady state when the input voltage changes; a current sampling circuit is provided at the inductor connected to the converter to sample the inductor current ripple information and convert it into a voltage signal to serve as the input signal for the transient detection circuit and the fixed on-time generation circuit input signals for the transient detection circuit and the fixed on-time generation circuit;

wherein the output voltage is sampled through a voltage divider network and then adjusted with the reference voltage by a high bandwidth op-amp, and is also used as the input signal for the fixed on-time generation circuit and the transient detection circuit; the transient detection circuit compares the current ripple information with the output voltage information, and when a dramatic increase in load occurs, the modulator is controlled to force the upper tube on until it is detected again; $V_{comp}>V_{iL}$, at which point the modulator is controlled to force the upper tube on until it is redetected $V_{comp}\leq V_{iL}$ the modulator is then controlled to turn the upper tube on forcibly until it is detected again, restoring steady-state COT control, thus achieving an approximate single-cycle transient response; where $V_{comp}$ is the error amplification signal of the output voltage after the operational amplifier, and $V_{iL}$ is the ripple voltage signal obtained from the inductor current sampling and conversion.

2. The blockchain and human characteristics intelligence recognition-based appointment-based elderly care system of claim 1:

wherein the central processing module matches the face image information captured by the video capture module, specifically comprising the steps of:

1.1) data acquisition step: the video acquisition module acquires the original image of the wearer's human face features; the acquired original image is de-noised, then color-corrected, followed by face alignment, and finally cropped to obtain a pure face image;

1.2) feature extraction step: obtain the data set after processing in step 1.1) and use $I^i$ denote the ith image of P*Q, and perform LBP on each image to obtain a new image $$I_i^{LBP};$$

changed the $$I_i^{LBP}$$

LBP is applied to each image to obtain a new image; the image is stretched into vector form and multiple images are combined into a single image matrix to generate the LBP feature space $$\{x_1^{LBP}, x_2^{LBP} \ldots x_N^{LBP}\};$$

perform mean normalisation on the images and obtain $$x_{avg}^{LBP} = \frac{1}{N}\sum_{i=1}^{N} x_i^{LBP}$$

mean value of all images to generate the mean face meanface, and subtract the mean value of all images; if the image dimension is not high at this time, find its eigenvalue and eigenvector by the covariance matrix; if the image dimension is too high at this time, first calculate the $X^T \cdot X$ The eigenvalues and eigenvectors of the matrix, due to the left multiplication of $X^T \cdot X \cdot v=\lambda \cdot v$, perform a left multiplication matrix X, we get $X \cdot X^T \cdot (X \cdot v)=\lambda \cdot (X \cdot v)$, which gives that the eigenvalues of $X \cdot X^T$ are the eigenvalues of $X^T \cdot X$ and the eigenvectors are $u=X \cdot v$;

1.3) operational processing step: sort the feature values in step 1.2) from largest to smallest, and take the first k feature values, and the corresponding first k feature vectors $(u_1, u_2, u_3 \ldots u_k)$ as the LBP Eigenface, at which point each feature vector is a feature face; thus through the new k-dimensional subspace, the original high-dimensional vector can be passed through the low-dimensional $(w_1, w_2, w_3 \ldots w_k)$ representation of a face; where the eigenvectors are P*Q dimensional vectors, the calculation $w_k$ the following equation:

$$w_k = u_k^T(x_i^{LBP} - x_{avg}^{LBP}).$$

3. The blockchain and human characteristics intelligence recognition-based appointment-based elderly care system of claim 2:

wherein the denoising process of the image in step 1.1) uses median filtering, where the median filtering is a process of arranging the pixel values in order of size in a convolution frame, selecting the middle pixel value as the filtered pixel value, and cycling through all the pixel values in turn to produce the filtered image;

color correction using histogram correction, where more concentrated areas of the histogram are split and stretched, and more dispersed areas are combined and compressed so that the pixels within a range are approximately the same;

face alignment acquires images containing pure face sizes by key point recognition, transforming the face.

4. The blockchain and human characteristics intelligence recognition-based appointment-based elderly care system of claim 3:

wherein face alignment uses face recognition for face keypoint detection to obtain 68 keypoints; then the face is rotated according to the angle between the left and right eye center coordinates and the horizontal direction to align it vertically, after alignment, and the obtained other face coordinates are similarly rotated; then the width of the face in the horizontal direction is obtained according to the leftmost and rightmost coordinates of the lower jaw respectively after alignment, and then the vertical length of the face is obtained from the ratio of the center of the eyes to the center of the mouth.

5. The blockchain and human characteristics intelligence recognition-based appointment-based elderly care system of claim 2:

wherein a face is reconstructed by meanface+u·k, i.e. the average face+feature vector*reduced dimensional coordinates for representation.

6. The blockchain and human characteristics intelligence recognition-based appointment-based elderly care system of claim 1:

wherein the power supply module further comprising a driver circuit, a converter B, an inductor L, a capacitor C, a resistor R and a MOS tube;

the input of converter B is connected to the input voltage sampling circuit, and the input voltage sampling circuit is connected to the fixed on-time generation circuit, and the other input of converter B is connected to MOS tube S1, and the gate of MOS tube S1 is connected to the driver circuit; the output of converter B is connected to MOS tube S2 and MOS tube S3, and the gate of MOS tube S2 and the gate of MOS tube S3 are connected to the driver circuit; the source of MOS tube S3 is connected to inductor L, and the output sampling circuit is connected to the transient detection circuit and the fixed on-time generation circuit, and the fixed on-time generation circuit is connected to the driver circuit; the source of MOS tube S3 is connected to inductor L, and the output sampling circuit is connected to inductor L; the output sampling circuit is connected to the transient detection circuit and the fixed on-time generation circuit, and the fixed on-time generation circuit is connected to the driver circuit and the transient detection circuit;

wherein, one end of the inductor L is connected to one end of the inductor C and one end of the resistor R, the other end of the inductor C and the other end of the resistor R are grounded together, and the inductor C and the resistor R form a voltage divider network.

7. The blockchain and human characteristics intelligence recognition-based appointment-based elderly care system of claim 6:

wherein the output sampling circuit comprises a resistor, a capacitor, an operational amplifier and a comparator;

one end of capacitor Cs is connected to one end of resistor R3 and the other end of capacitor Cs is connected to one end of resistor R1 and is used as the two differential sampling input pins for the output sampling circuit;

the other end of resistor R1 is connected to one end of resistor R2, the positive terminal of telecom amplifier U2, and the other end of resistor R2 is grounded; the other end of resistor R3 is connected to one end of resistor R4, the negative terminal of telecom amplifier U2, and the other end of resistor R4 is used as an external pin together with the output of telecom amplifier U2 and is connected to one end of comparator U3;

the other end of resistor RFBT is connected to one end of resistor R5, one end of operational amplifier U5 as the sampling input pin of the output sampling circuit, the other end of operational amplifier U5 is connected to the reference voltage Vref, the other end of resistor R5 is connected to one end of capacitor C1, the other end of capacitor C1 is connected as an external pin together with the output of operational amplifier U5 and is connected to the other end of comparator U3, the output of comparator U3 is used as the other external pin.

8. The blockchain and human characteristics intelligence recognition-based appointment-based elderly care system of claim 7:

wherein the output sampling circuit is externally designed with one end of the inductor L connected to one end of the resistor Rs, the other end of the inductor L connected to one end of the capacitor Cs, one end of the capacitor Cout, and one end of the resistor RFBT, and the other end of the resistor Rs connected to the other end of the capacitor Cs; the other end of the capacitor Cout is grounded together with one end of the resistor RFBB, and the other end of the resistor RFBB is connected to the resistor the other end of the RFBT is connected to the other end of the RFBT;

the output sampling circuit consists of two parts: inductor current and output voltage sampling; the inductor current sampling design needs to satisfy the following equation:

$$R_s \cdot C_s = i_L / R_{DCR}$$

where $R_{DCR}$ is the inductor DC resistance, which converts the inductor current into $C_s$ voltage on the inductor and connects it to the two inputs of the telecom amplifier $U_2$, the telecom amplifier $U_2$ converts the differential signal to output relative to the reference ground and connects it to the inverting input of the comparator $U_3$ and the input of the bias voltage.

* * * * *